US00PP23843P2

(12) United States Plant Patent
Giesen

(10) Patent No.: US PP23,843 P2
(45) Date of Patent: Aug. 20, 2013

(54) *LOBELIA* PLANT NAMED 'LOBZ0001'

(50) Latin Name: *Lobelia erinus*
Varietal Denomination: LOBZ001

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 114 days.

(21) Appl. No.: 13/317,195

(22) Filed: Oct. 12, 2011

(51) Int. Cl.
*A01H 5/00* (2006.01)

(52) U.S. Cl.
USPC ..... Plt./451

(58) Field of Classification Search
USPC ..... Plt./451
See application file for complete search history.

*Primary Examiner* — June Hwu
(74) *Attorney, Agent, or Firm* — Joshua L. Price

(57) ABSTRACT

A new *Lobelia* plant named 'LOBZ0001' particularly distinguished by the purple-violet colored flowers with distinct purple markings on the lower petals, medium green leaves, strong stems, freely branching, and semi-upright to semi-trailing plant habit.

1 Drawing Sheet

Latin name of the genus and species of the plant claimed: *Lobelia erinus.*

Varietal denomination: 'LOBZ0001'.

BACKGROUND OF THE NEW PLANT

The present invention comprises a new and distinct cultivar of *Lobelia*, botanically known as *Lobelia erinus* and hereinafter referred to by the cultivar name 'LOBZ0001'.

'LOBZ0001' is a product of a planned breeding program. The new cultivar has purple-violet colored flowers with distinct purple markings on the lower petals, medium green leaves, strong stems, freely branching, and semi-upright to semi-trailing plant habit.

'LOBZ0001' originated from a hybridization made in March 2006 in Andijk, Netherlands. The female parent was the proprietary unpatented plant designated 'LOB05-216-3', having larger flowers, somewhat less deep green foliage and thinner stems.

The male parent of 'LOBZ0001' was the proprietary, unpatented plant designated 'LOB05-218-11', having smaller petals, foliage with stronger pubescence, and more spreading, less trailing plant habit.

The resulting seeds were sown June 2006 and 'LOBZ0001' was selected as one flowering plant within the progeny of the stated cross in August 2006 in a controlled environment in Andijk, Netherlands.

The first act of asexual reproduction of 'LOBZ0001' was accomplished when vegetative cuttings were propagated from the initial selection in the fall of 2006 in a controlled environment in Andijk, Netherlands.

BRIEF SUMMARY OF THE INVENTION

Horticultural examination of plants grown from cuttings of the plant initiated in the spring of 2007 in Andijk, Netherlands, and continuing thereafter, has demonstrated that the combination of characteristics as herein disclosed for 'LOBZ0001' are firmly fixed and are retained through successive generations of asexual reproduction.

'LOBZ0001' has not been observed under all possible environmental conditions. The phenotype may vary significantly with variations in environment such as temperature, light intensity and day length.

Plant Breeder's rights for this cultivar were applied for in Canada on Dec. 24, 2010; #10-7138 and in the European Union on Oct. 15, 2010, #2010/1757. 'LOBZ0001' has not been made publicly available more than one year prior to the filing of this application.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

The accompanying photographic drawing shows typical flower and foliage characteristics of 'LOBZ0001' with colors being as true as possible with an illustration of this type.

Figure 1:
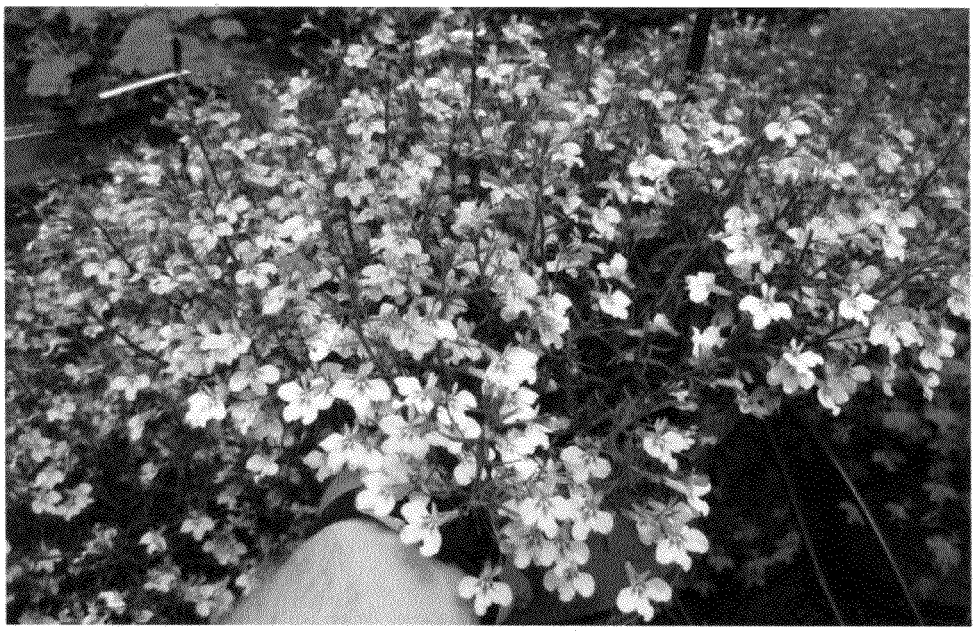
Figure 2:
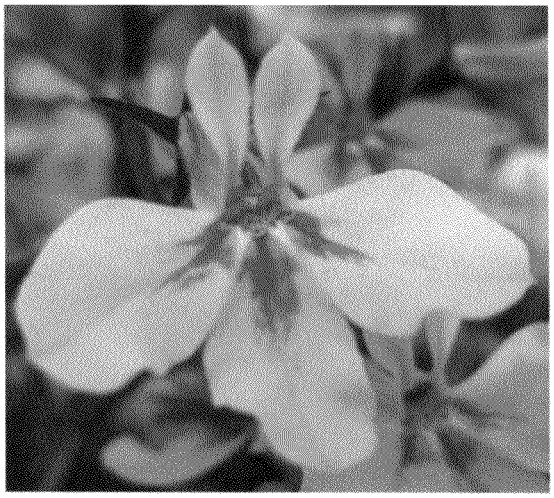

The photographic drawing shows in FIG. 1. a flowering plant of the new variety and in FIG. 2. a close-up of the flowers.

DETAILED BOTANICAL DESCRIPTION

The aforementioned photographs, plant measurements and descriptions were taken in Andijk, Netherlands in May 2011 on 12-14 week-old plants that were growing in 10 cm pots in a greenhouse at relatively cool conditions of about 14-16 degrees C. minimum temperature. Plants received 1 terminal pinch of the apices at an early age.

Color chart used: The Royal Horticultural Society Colour Chart (R.H.S.), 2001.

TABLE 1

DIFFERENCE BETWEEN THE NEW VARIETY 'LOBZ0001' AND A SIMILAR VARIETY

| | 'LOBZ0001' | 'Lobantis' (U.S. Plant Pat. No. 18,198) |
|---|---|---|
| Main flower color: | Purple-violet | Purple |
| Plant growth habit: | A bit more trailing | A bit more upright and mounding |
| Stem thickness: | Thicker | Very thin |

Plant:

*Growth and habit.*—Vigorous growth; dense and freely branched with short internodes.

*Form.*—Initially spreading, later semi-trailing.

*Height.*—About 5.0 cm (from top of soil).

*Height (inflorescence included).*—About 10.0 cm.

*Width (horizontal diameter).*—30.0 cm.

Roots:

*Time to initiate and develop roots.*—21-28 days at 68° F.-74° F.

*Root description.*—Fibrous and freely branching.

Foliage:

*Arrangement.*—Alternate; sessile to slightly decurrent.

*Immature leaf, color upper surface.*—RHS 137D or RHS 138A.

*Immature leaf, color lower surface.*—RHS 137D.

*Mature color upper surface.*—RHS 137C.

*Mature color lower surface.*—RHS 137D and RHS 187B.

*Leaf length.*—5.0 cm.

*Leaf width.*—2.5 cm.

*Shape.*—Oblanceolate or elliptic at lower portion of stems; ligulate at mid portion of flowering stems.

*Apex shape.*—Apiculate.

*Base shape.*—Attenuate.

*Margin shape.*—Dentate.

*Texture.*—Hairs on both surfaces.

*Venation type.*—Pinnate.

*Venation color, upper surface.*—RHS 144C.

*Venation color, lower surface.*—RHS 144C.

Stem:

*Color.*—RHS 139B with RHS 187A at more terminal end.

*Quantity of main branches per plant.*—10-12.

*Stem length.*—13 cm.

*Diameter.*—0.3 cm.

*Internode length.*—1.5 cm.

*Texture.*—Covered with hair.

Peduncle:

*Color.*—RHS 139B.

*Length.*—About 5.0-11.0 cm.

*Diameter.*—0.3 cm.

*Texture.*—Covered with short hair.

Pedicel:

*Color.*—RHS 139B.

*Length.*—1.6-2.7 cm.

*Diameter.*—0.1 cm.

*Texture.*—Pubescent.

Inflorescence:

*Type of inflorescence.*—Raceme, composed of single flowers in an alternate arrangement with one flower per node, subtended by a little leaflet.

*Blooming habit.*—Continuous through the growing season from spring to fall.

*Quantity of inflorescences per plant.*—About 150.

*Lastingness of individual blooms on the plant.*—About 5-7 days, depending on temperature.

*Fragrance.*—None.

*Inflorescence length.*—About 5.0-8.0 cm.

*Inflorescence diameter.*—5.5-7.5 cm.

*Flowers per raceme.*—Most often 13-15 with 3-5 buds.

Bud (just when starting to show color):

*Color.*—RHS N80D.

*Length.*—1.1 cm.

*Diameter.*—0.4 cm.

*Shape.*—Elongated, becoming slightly wider towards the upper end.

Flower:

*Corolla type.*—Single, zygomorphic; upper lip is formed by two small lobes, lower lip has three larger lobes; lobes are fused at the base forming a relatively long funnel-shaped tube.

*Immature inflorescence.*—Diameter of flower: 1.4-1.5 cm. Main color upper surface: RHS N80C, with a weak coloring of about RHS N80B at the midvein and base of petals. Main color lower surface: RHS N87D to RHS N88D.

*Mature inflorescence.*—Depth of flower: 1.7 cm. Diameter of flower: 1.7 cm. Vertical length of flower: 1.4 cm.

*Upper petals.*—Color, upper surface: Shades closest to RHS N82D, with a very weak or sometimes indistinct midvein and petal base marking of about RHS N80B; fading to shades closer to RHS N80D and some even closer to RHS 84D. Color, lower surface: RHS N82D. Length (from the corolla opening): 0.6 cm. Width: 0.2 cm.

*Lower petals.*—Color upper surface: Shades closest to RHS N82D with a somewhat distinct spot of RHS N79C; and a fine line RHS N80B; fading to shades closer to RHS 77D and RHS 84D. Color, lower surface: RHS N80C. Length (from the corolla opening): 1.1 cm. Width: 0.6 cm.

*All petals.*—Petal shape: Obovate. Petal apex: Rounded. Petal base: Fused. Margin: Entire. Texture: Upper surface glabrous, underside pubescent. Corolla tube, color outside surface: Closest to RHS N80C on the upper facing side, and RHS 77C on the underside. Corolla tube, color inner surface: RHS 76A to RHS 76B with 4-5 weak spots, near the throat of RHS N80D. Corolla tube length: 0.8 cm. Corolla tube width: 0.3 cm.

Calyx:

*Quantity and form.*—5 sepals in a whorl, slanting outwards.

*Sepal color.*—RHS 137C.

*Sepal length.*—0.9 cm.

*Width.*—0.2 cm.

*Shape.*—Subulate.

*Apex.*—Pointed, acute.

*Base.*—Fused.

*Texture, upper surface.*—Glabrous.

*Lower surface.*—Covered with short hair along the edges.

Reproductive organs:

*Stamens.*—5. Filament color: RHS N82C. Anther color: RHS 197C. Filament length: 0.5 cm. Diameter: Less than 0.1 cm. Anther length: 0.2 cm. Pollen amount: Little. Pollen color: RHS 4D.

*Pistil.*—1. Length: Approximately 1.5-1.8 cm. Stigma color: RHS N92B. Style color: RHS 144C.

Fruit and seed set: Fruit and seed set has not been observed on this hybrid.

Disease and insect resistance: Disease and insect resistance has not been observed on this hybrid.

The invention claimed is:

1. A new and distinct cultivar of *Lobelia* plant named 'LOBZ0001' substantially as illustrated and described herein.

* * * * *

UNITED STATES PATENT AND TRADEMARK OFFICE

CERTIFICATE OF CORRECTION

PATENT NO. : PP23,843 P2
APPLICATION NO. : 13/317195
DATED : August 20, 2013
INVENTOR(S) : Giesen It is certified that error appears in the above-identified patent and that said Letters Patent is hereby corrected as shown below:

Title Page:

At (50), delete "LOBZ001" and insert therefor --LOBZ0001--

Signed and Sealed this
Eighth Day of October, 2013

Teresa Stanek Rea
*Deputy Director of the United States Patent and Trademark Office*